US009237963B2

(12) United States Patent
Carrier

(10) Patent No.: US 9,237,963 B2
(45) Date of Patent: Jan. 19, 2016

(54) RAPID EXTRICATION DEVICE

(71) Applicant: Allen Carrier, Goshen, OH (US)

(72) Inventor: Allen Carrier, Goshen, OH (US)

(*) Notice: Subject to any disclaimer, the term of this patent is extended or adjusted under 35 U.S.C. 154(b) by 61 days.

(21) Appl. No.: 13/853,278

(22) Filed: Mar. 29, 2013

(65) Prior Publication Data

US 2013/0312772 A1    Nov. 28, 2013

Related U.S. Application Data

(60) Provisional application No. 61/617,250, filed on Mar. 29, 2012.

(51) Int. Cl.
*A61F 5/37* (2006.01)
*A61G 1/044* (2006.01)
*A61G 1/01* (2006.01)

(52) U.S. Cl.
CPC ............... *A61F 5/3776* (2013.01); *A61G 1/01* (2013.01); *A61G 1/044* (2013.01)

(58) Field of Classification Search
CPC ......... A61G 1/01; A61G 1/013; A61G 1/044; A61G 1/04; A61G 2210/50; A61G 7/0504; A61G 1/00; A61G 1/017; A61G 1/048; A61G 7/1023; A61G 7/1026; A41D 13/0531; A61B 2562/0219; A61B 2562/028; A61F 5/05883
USPC .................. 129/845; 128/869–870, 845, 876; 5/611, 625, 627, 628, 637
See application file for complete search history.

(56) References Cited

U.S. PATENT DOCUMENTS

| | | | |
|---|---|---|---|
| 3,620,211 A | 11/1971 | Goddell et al. | |
| 4,473,912 A | 10/1984 | Scheidel et al. | |
| 4,601,075 A | 7/1986 | Smith | |
| 4,895,173 A | 1/1990 | Brault et al. | |
| 4,945,583 A | 8/1990 | Schnitzler | |
| 5,058,575 A | 10/1991 | Anderson | |
| 5,161,275 A | 11/1992 | Simpson et al. | |
| 5,317,770 A | 6/1994 | Sakurai | |
| 5,375,277 A * | 12/1994 | Carr et al. ......................... | 5/625 |
| 5,729,850 A | 3/1998 | Eskeli | |
| 5,745,938 A | 5/1998 | Bartley et al. | |
| 5,803,087 A | 9/1998 | Thompson | |
| 5,947,515 A | 9/1999 | Fitch | |
| 5,950,627 A | 9/1999 | Bologovsky et al. | |
| 6,061,853 A | 5/2000 | Laaksonen et al. | |
| 6,227,201 B1 * | 5/2001 | Ferko, III ...................... | 128/869 |
| 6,363,936 B1 * | 4/2002 | McCormick et al. ......... | 128/870 |
| 6,526,983 B1 | 3/2003 | Pizzi Spadoni | |
| 6,857,143 B2 | 2/2005 | McNulty | |

(Continued)

*Primary Examiner* — Michael Brown
(74) *Attorney, Agent, or Firm* — Hasse & Nesbitt LLC; Daniel F. Nesbitt

(57) ABSTRACT

A light-weight rigid extrication board having an elongated central section and in-turned sidewalls including one or more planar sections, extending from both sides of the central section, having a plurality of openings formed along the length of both sidewalls, that include an upper opening at the top end of the board, a bottom opening at the bottom end of the board, and an intermediate opening. Straps are secured to each of the openings in the sidewalls, each strap having a fastening buckle at the end of the strap for temporary fastening to one of the other straps. A hoop-shaped halo extends from a top end of the board. The extrication board is slipped behind the driver and the straps secure the extrication board to the back of the driver while seated. Tape can be used to temporarily secure the driver's helmet to the halo during extrication and transport.

6 Claims, 3 Drawing Sheets

(56) References Cited

U.S. PATENT DOCUMENTS

| | | | |
|---|---|---|---|
| 6,871,368 B2 * | 3/2005 | Calkin | 5/628 |
| 7,017,209 B1 | 3/2006 | De Jong et al. | |
| 7,165,278 B2 | 1/2007 | Tomcany et al. | |
| 7,337,484 B2 * | 3/2008 | Cox | 5/625 |
| 7,360,543 B1 | 4/2008 | Coleman et al. | |
| 7,428,762 B1 | 9/2008 | Kalies | |
| 7,726,668 B2 | 6/2010 | Sieb et al. | |
| 7,748,062 B2 | 7/2010 | McNulty | |
| 7,810,820 B2 | 10/2010 | Wolf et al. | |
| 2002/0149253 A1 | 10/2002 | MacDonald | |

* cited by examiner

RAPID EXTRICATION DEVICE

CROSS REFERENCE TO RELATED APPLICATIONS

This application claims the benefit of U.S. Provisional application 61/617,250, filed Mar. 29, 2012, the disclosure of which is incorporated by reference in its entirety.

TECHNICAL FIELD

The present invention relates a safety device for extracting an injured person from a vehicle.

BACKGROUND OF THE INVENTION

Accidents and resulting injuries are an all too common occurrence for race car drivers. Given the high speeds involved in car racing, many accidents result in which the driver is too badly injured or traumatized to extricate himself from the vehicle following the crash. Of course, time is of the essence after an accident to commence medical treatment of the injured driver and also to quickly remove the driver from the vicinity of the vehicle in case of fire or explosion. These accidents sometimes involve injuries to the head or spinal cord of the driver. In such situations, it is imperative to stabilize the driver's head and spinal cord as the driver is removed from the vehicle to prevent or minimize the risk of paralysis or further permanent injury to the driver.

SUMMARY OF THE INVENTION

The present invention provides a device and method for rapidly extricating a driver from a seat of a vehicle. An aspect of the device is a design and configuration that allows a rescue worker to slip or slide the device into position behind the back and head of the driver while still seated into the driver's seat of the vehicle, between the driver's back and the seatback. The design of the device includes a rigid structure that will hold its shape while being inserted behind the driver, and during extrication of the driver, after the driver has been secured to the device. The design also includes a bottom edge that is rigid and sufficiently thin to be slid in behind the drive, yet sufficiently thick enough not to snag or catch into the driver's clothing or the driver's seat while positioning the device behind the driver.

The device also includes a U-shaped halo extending from the top end of the board, to which the head can be secured during extrication from the vehicle and/or transport of the driver to a medical vehicle or a medical facility. If the driver has a helmet on, the helmet can be secured to the halo, for example with duct tape. If the helmet has been removed, the driver's head can be secure, for example with suitable adhesive tape or with velcro straps.

Another aspect of the device is turned-in sidewalls that allow the device to conform to the shape of the seatback of a driver's seat in a conventional stock racing car and in another vehicle. Another aspect of the device that it is light weight and ease of handle.

The present invention provide a light-weight rigid extrication board including an elongated central section and in-turned sidewalls extending from both sides of the central section, one or more securement straps extending from both of the sidewalls, and including a hoop-shaped bar extending from a top end of the board.

The device and method provide a very rapid extrication of the driver form the vehicle with due care for the health and safety of the driver.

BRIEF DESCRIPTION OF THE FIGURES

The invention will be more clearly understood from the following detailed description of representative embodiments thereof read in conjunction with the accompanying drawings that form a part of this disclosure.

DETAILED DESCRIPTION OF THE INVENTION

Figure 1:
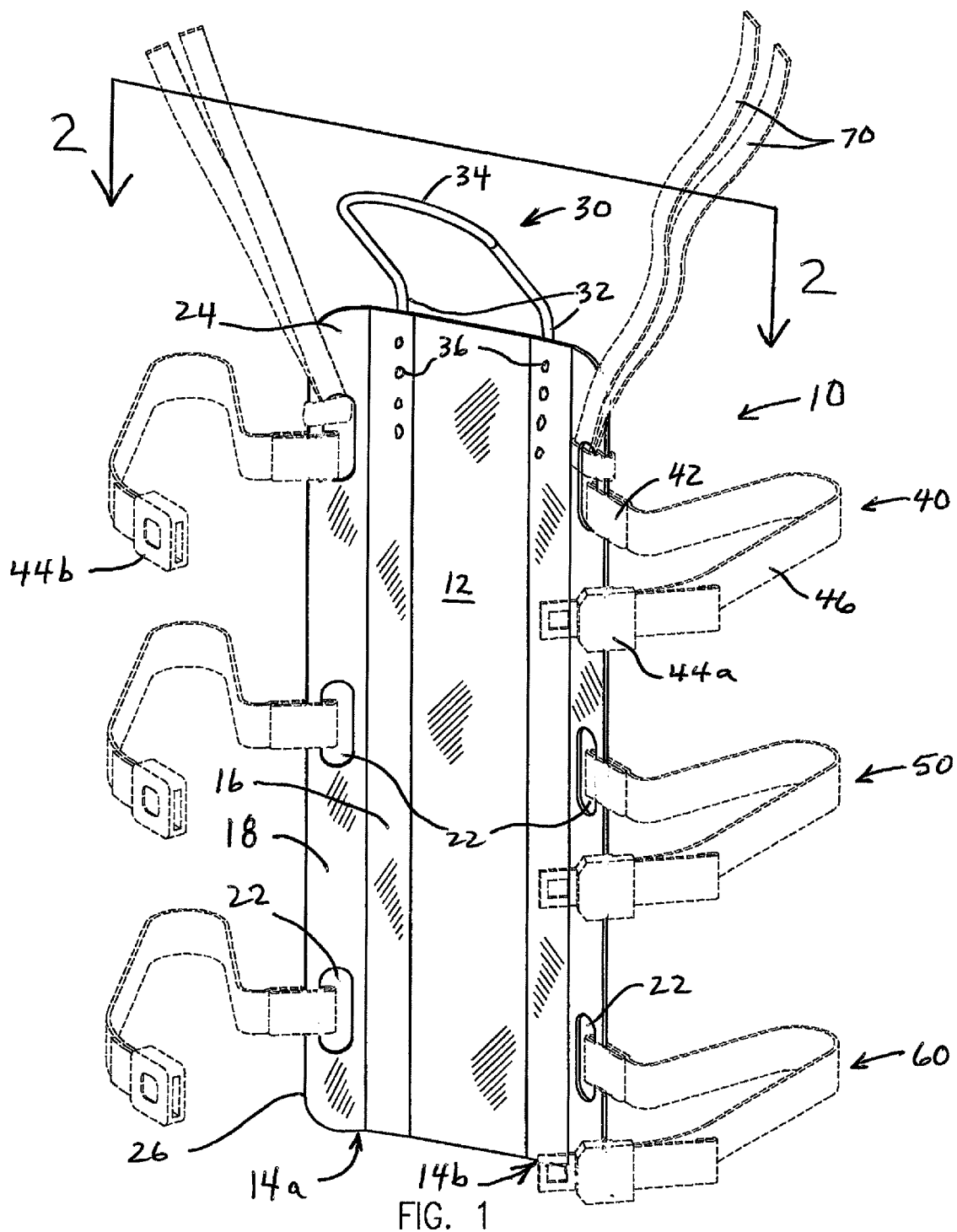
FIG. 1 shows a perspective view of the extrication device of the present invention.
Figure 2:
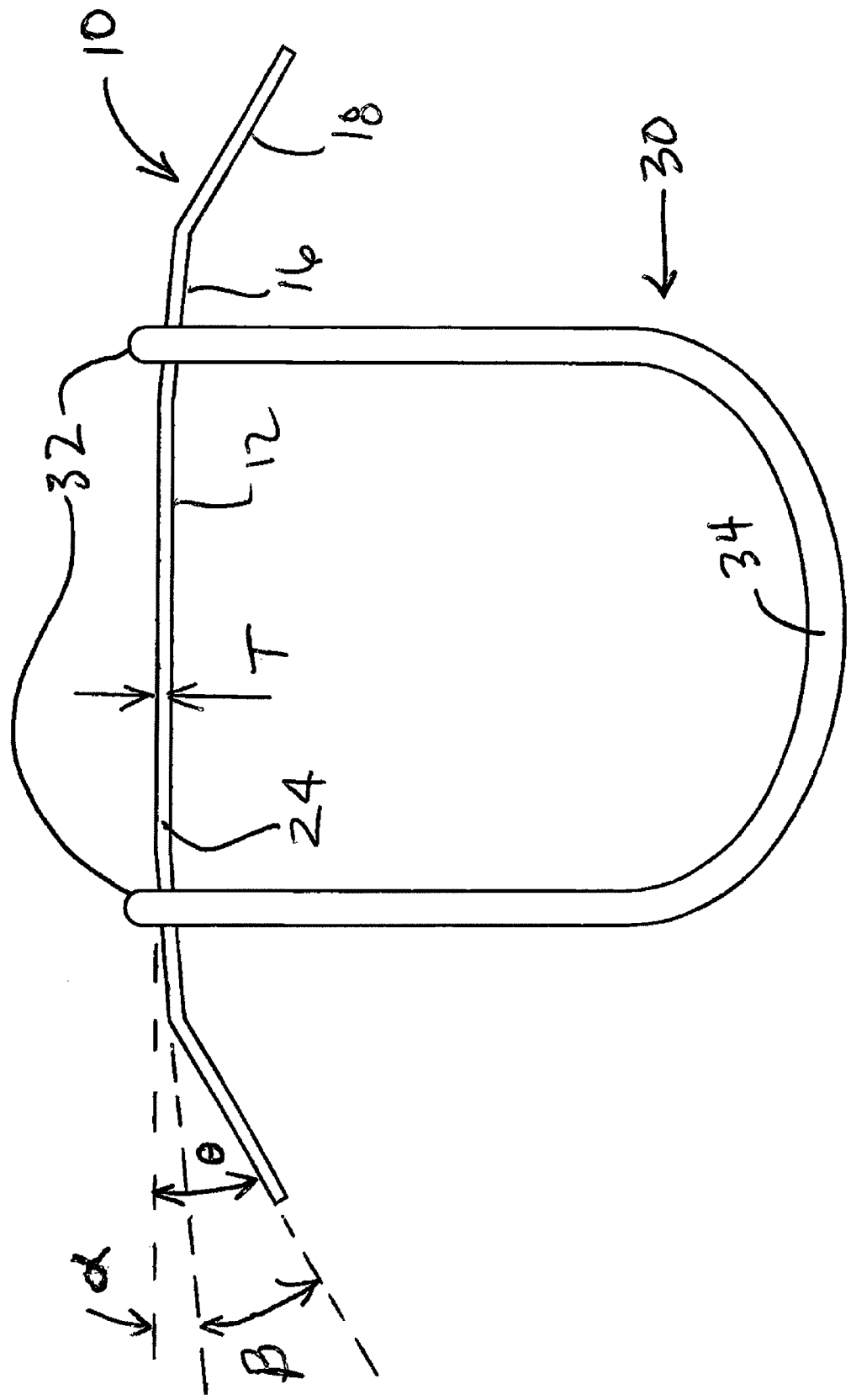
FIG. 2 shows the top views of the device, viewed along line 2-2 of FIG. 1.
Figure 3:
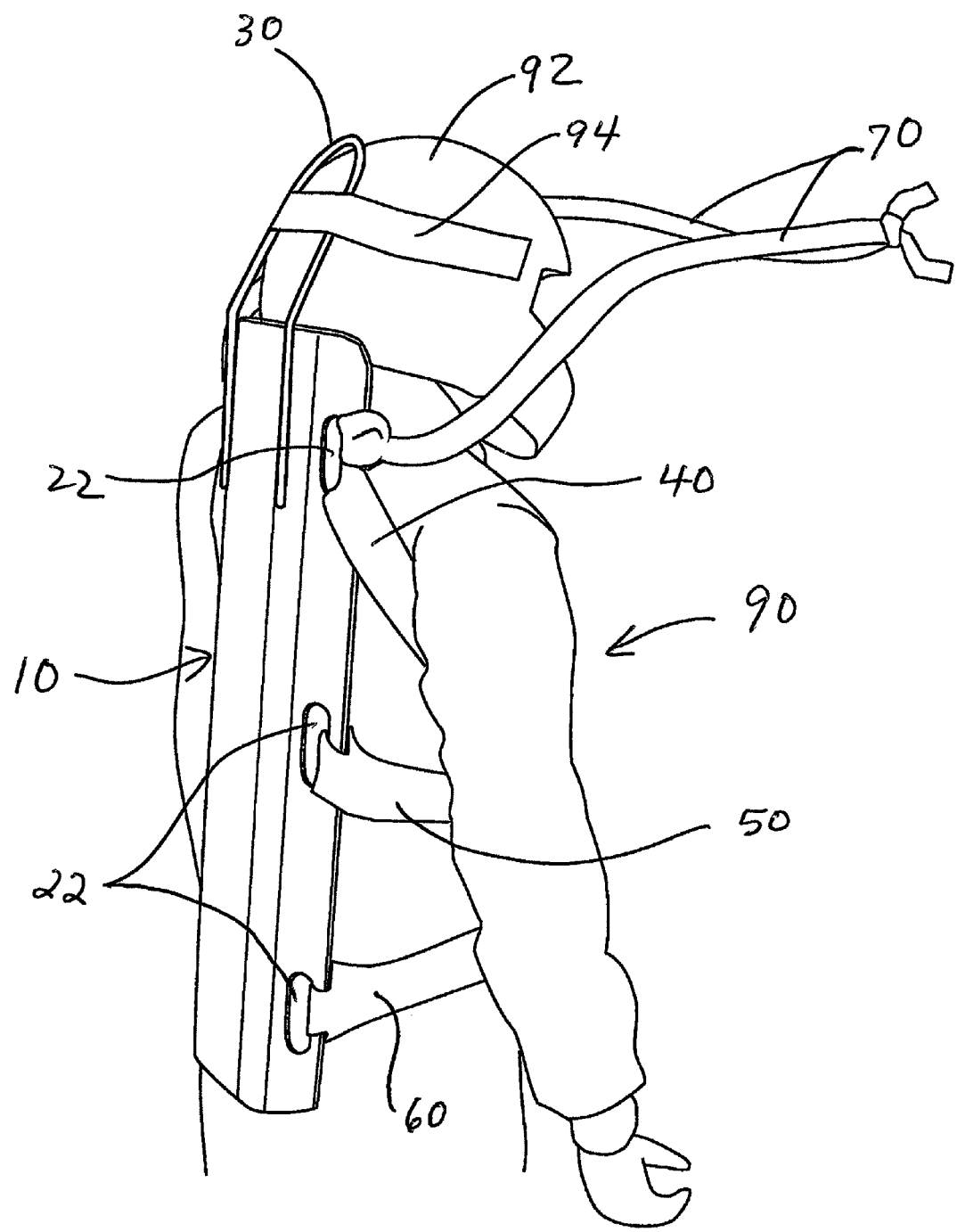
FIG. 3 shows a view of the extrication device secured to the back of a driver.

FIGS. 1-3 shows a light-weight rigid extrication board including an elongated central section and in-turned sidewalls extending from both sides of the central section, one or more securement straps extending from both of the sidewalls, and including a hoop-shaped bar extending from a top end of the board.

Extrication board 10 includes an elongated central section 12 having a length of about the length of a driver's back, and sidewalls 14a and 14b that extend from both sides of the central section, and which are turning inward (as shown in FIG. 2). The turned-in sidewalls 14 allow the board 10 to conform to the back and sides of a driver 90, and to the backseat of the driver's seat (not shown), which is similarly contoured to the body of the driver. As shown in FIG. 2, the sidewalls 14a, 14b can have one or more straight or planar sections 16 and 18, although the turned-in sidewalls can be curved, or a combination of curved and planar sections. The first section 16 can turn inward from the central section 12 about 3-10 degrees ($\alpha$), such as 5 degrees, and the second section 18 can turn inward from the first section 16 about 20-30 degrees ($\beta$), such as 25 degrees. The overall turn inward from of the outer section is about 23-40 degrees ($\theta$), such as about 28-32 degrees. Typically the overall width of the board 10 is about 8-12 inches, typically about 8-10 inches, with a board length of about 22-26 inches. The central section typically has a width of about 4-6 inches.

A plurality of securement straps 40, 50, 60 and 70 extend from both of the sidewalls 14a and 14b. The straps are secured at one end to the board, and include a fastener at the distal end for securing to another portion of the board 10, or to another strap. In the illustrated embodiment, the board includes opposed oval-shaped openings 22 along both sidewalls, including openings 22 near the upper end 24, openings 22 near the bottom end 26, and openings intermediate the length of the board. The openings 22 provide a means for grasping and handling the board. A proximal end 42 of the straps can be tied to sidewall at the opening, or can be secured by threading the proximal end through the opening and fastening it to the body of the strap using stitching or other well known securing means. At the distal end of the straps is a second fastener, illustrated as the male and female components of a buckle with an adjustment for the length 46 of the strap. The second fastener can also include the complimentary components of a mechanical fastener, commonly referred to as velcro, or other equivalent fastening means.

As shown in FIG. 3, after the board 10 has been placed behind the back of a driver 90, an upper strap 40 on a first side is positioned over the shoulder of the driver and fastened to an intermediate strap 50 that has been positioned under the armpit of the driver on the other side. The upper strap 40 on the other side is then positioned over the opposite shoulder and fastened to the intermediate strap 50 under the armpit of the driver on the first side, so that the straps cross over the chest of the driver. The lower straps 60 are positioned and fastened around the waist or lower torso of the driver.

A halo or hoop-shaped rod 30 is fixed to the top end 24 of the board 10. The halo 30 is illustrated as a u-shaped rod with a curved outer portion 34 and two extending legs 32 that are secured to the back of the extrication board 10, such as with a mechanical fastener of well-known type (for example, a bolt or rivet). The halo rod can be a metal or non-metal material, including a steel or aluminum material, for example, with sufficient rigidity and strength to maintain its shape if used as a means for lifting the body of the driver secured to the board, or when the helmet 92 of the driver 90 is secured to the halo 30. A 5/16-inch diameter steel rod is sufficient.

As shown in FIG. 2, the halo can extend from the top end 24 of the board 10 at an angle, relative to the plane of the central section 12, of about 10-20 degrees, such as 15 degrees, and up to 45 degrees. This angle is selected to maintain the neck and back of the driver, with the helmet 92, in an appropriate alignment with the board 10.

As shown in FIG. 3, once the board 10 is secured to the back of the driver 90, tape 94, such as adhesive tape, or another securement, such as mechanical straps commonly referred to as velcro, can be used to temporarily secure the helmet 92 on the driver's head to the halo 30 during the extrication of the driver from the vehicle. Extrication of the driver, typically by lifting the driver up out of the seat and through an opening that has been made in the roof of the vehicle, can include lifting up on the halo 30, or by using additional lifting straps 70 secured to the two upper openings 22.

The extrication board 10 is typically made of a rigid, light-weight material, including a lightweight metal that can include aluminum, titanium, or a lightweight thermoplastic that can include polycarbonate. The thickness T of the board material should be sufficiently thick to maintain the rigidity of the extrication board as it is being inserted behind a driver, between the seatback of the driver's seat and the driver, yet as thin as possible to ensure a light weight and for fitting between the driver and the seatback. An aluminum plate of about 1/8 inch thick is suitable. The bottom edge of the board should also be rounded or have a width that prevents the edge from snagging or grabbing at the clothing of the driver during insertion.

The present invention also includes a method of extricating a driver from a driver's seat of a vehicle, after an opening has been made in the roof of the vehicle to give above access to the driver and to the seatback of the driver's seat, including the steps of:—providing the rigid extrication device of the invention as described herein,—sliding the board at the lower end between the seatback and the back of the driver, until the lower of the board is proximate the hips of the driver,—fastening together the buckles of the opposed lower straps around the waist or lower torso of the driver,—crossing over the opposed upper and intermediate straps, over the shoulder and under the armpits of the driver, and fastening the opposite-side upper and intermediate buckles,—optionally securing the head of the driver, or optionally the helmet of the driver, to the halo, including with tape, and—lifting the board secured to the back of the driver through the opening of the vehicle, including employing lifting straps attached to the upper openings in the board. If the driver is unconscious, the crossing straps can be placed over the outside of the arms to secure the river while being lifted from seat.

The Rapid Extrication Device (RED) is specially designed for the rapid extrication of race car drivers from their race car vehicle. The device can be designed for close-quarter extrication of drivers from their containment seats. Presently 75% of race cars are now equipped with containment seats, which are formed to the contour of the driver's body. With these seats, a backboard which is generally used by fire and EMS crews just will not work, since they are too long and too wide. The RED fits inside the seat between the seat back and the drive, and conforms to the drivers C-spine. Once secured to the driver, the driver can be lifted straight up out of his "cocoon" or cockpit of the race vehicle by a rescue crew. The driver's legs can be assisted by a rescue crew member as the driver is positioned onto the squad's conventional backboard. The RED device can then be removed by the squad, and driver secured to the conventional backboard with full c-spine precautions.

I claim:

1. A light-weight rigid extrication board for extracting a driver from a driver's seat having a seatback, including an elongated planar central section and an in-turned sidewall extending laterally from both sides of the central section, the extrication board being made of a metal or thermoplastic material having a thickness sufficient to maintain its rigid shape as the extrication board is being inserted between the seatback and the driver, one or more securement straps extending from both of the sidewalls, and including a hoop-shaped halo rod having a curved outer portion and two extending legs secured to the back of a top end of the board and extending at an angle from the plane of the central section, the extrication board having a length of a driver's back so that the halo rod is adjacent the driver's head when the extrication hoard is inserted between the seatback and the driver, the halo rod having sufficient rigidity to maintain its shape and position when used for lifting the driver or when securing a helmet of the driver to the halo rod.

2. The light-weight rigid extrication board according to claim 1, further including a plurality of openings formed along the length of both sidewalls, wherein the one or more straps are secured to each of the openings in the sidewalls, each strap having a fastener at a distal end of the strap.

3. The light-weight rigid extrication board according to claim 1, wherein the length of the extrication board is 22-26 inches.

4. The light-weight rigid extrication board according to claim 3, wherein the in-turned sidewall includes one or more planar sections.

5. A light-weight rigid extrication board including an elongated central section and in-turned sidewalls including one or more planar sections, extending from both sides of the central section, a plurality of openings formed along the length of both sidewalls, including an upper opening at the top end of the board, a bottom opening at the bottom end of the board, and an intermediate opening, and straps secured to each of the openings in the sidewalls, each strap having a fastener at a distal end of the strap for temporary fastening to one of the other straps, and including a hoop-shaped halo extending from a top end of the board and including a hoop-shaped halo rod having a curved outer portion and two extending legs secured to the back of a top end of the board and extending at an angle from the plane of the central section, the extrication board having a length of a driver's back so that the halo rod is adjacent the driver's head when the extrication board is inserted between the seatback and the driver, the halo rod having sufficient rigidity to maintain its shale and position when used for lifting the driver or when securing a helmet of the driver to the halo rod.

6. A method of extricating a driver from a driver's seat of a vehicle, after an opening has been made in the roof of the vehicle to give above access to the driver and to the seatback of the driver's seat, including the steps of:

providing the rigid extrication device according to claim 1, sliding the board at the lower end between the seatback and the back of the driver, until the lower of the board is proximate the hips of the driver, fastening together buckles of opposed lower straps around the waist or lower torso of the driver, crossing over opposed upper and intermediate straps, over the shoulder and under the armpits of the driver, and fastening opposite-side upper and intermediate buckles, optionally securing the head of the driver, or optionally the helmet of the driver, to the halo, and lifting the board secured to the back of the driver through the opening of the vehicle, including employing lifting straps attached to the upper openings in the board.

* * * * *